US005629407A

United States Patent [19]
Xiong et al.

[11] Patent Number: 5,629,407
[45] Date of Patent: May 13, 1997

[54] DNA ENCODING AN 18 KD CDK6 INHIBITING PROTEIN AND ANTIBODIES THERETO

[75] Inventors: Yue Xiong, Chapel Hill, N.C.; Kunliang Guan, Ann Arbor, Mich.

[73] Assignees: The University of Michigan, Ann Arbor, Mich.; The University of North Carolina at Chapel Hill, Chapel Hill, N.C.

[21] Appl. No.: 486,410

[22] Filed: Jun. 7, 1995

Related U.S. Application Data

[62] Division of Ser. No. 263,935, Jun. 21, 1994.

[51] Int. Cl.⁶ .................................................. C07K 16/00
[52] U.S. Cl. ........................... 530/387.1; 530/387.9; 530/387.7; 530/388.1; 530/388.22
[58] Field of Search ......................... 530/387.1, 387.7, 530/387.9, 388.1, 388.2, 389.1, 389.7

[56] References Cited

U.S. PATENT DOCUMENTS 5,302,706  4/1994  Smith ..................................... 536/23.1

OTHER PUBLICATIONS

A. Kamb et al; *A Cell Cycle Regulator Potentially Involved in Genesis of Many Tumor Types*, Science 264, pp. 436–440 (1994).

Jean Marx; *New Tumor Suppressor May Rival p53*; Science 264, pp. 344–345 (1994).

Jean Marx; *How p53 Suppresses Cell Growth*; Science 262, pp. 1644–1645 (1993).

Hui Zhang et al; *Proliferating Cell Nuclear Antigen and p21 Are Components of Multiple Cell Cycle Kinase Complexes*; Molecular Biology of the Cell, 4, pp. 897–906 (1993).

Yue Xiong et al; *p21 Is a Universal Inhibitor of Cyclin Kinases*; Nature 366, pp. 701–704 (1993).

Yue Xiong et al; *Subunit rearrangement of the cyclin–dependent kinases is associated with cellular transformation*; Genes & Development 7, pp. 1572–1583 (1993).

M. Serrano et al; *A new regulatory motif in cell–cycle control causing specific inhibition of cyclin D/CDK4*; Nature 366, pp. 704–707 (1993).

Yue Xiong et al; *D Type Cyclins Associate with Multiple Protein Kinases and the DNA Replication and Repair Factor PCNA*; Cell 71, pp. 505–514 (1992).

*Primary Examiner*—Marian C. Knode
*Assistant Examiner*—Yvonne Eyler
*Attorney, Agent, or Firm*—Bell, Seltzer, Park & Gibson

[57] ABSTRACT

A nucleic acid encoding a CDK inhibiting protein, particularly a CDK6 inhibiting protein, is selected from the group consisting of: (a) DNA having the nucleotide sequence given herein as SEQ ID NO:1 (which encodes the protein having the amino acid sequence given herein as SEQ ID NO:2), and which are refered to as $p18^{INK6}$; (b) nucleic acids which hybridize to DNA of (a) above and which encode a CDK inhibiting protein; and (c) nucleic acids which differs from the DNA of (a) or (b) above due to the degeneracy of the genetic code, and which encodes a CDK inhibiting protein encoded by a DNA of (a) or (b) above. Constructs containing such DNA, cells containing such constructs, proteins encoded by such DNA, antibodies which bind thereto, antisense oligonucleotides corresponding to such DNA, and methods of using the same are also disclosed.

6 Claims, No Drawings

DNA ENCODING AN 18 KD CDK6 INHIBITING PROTEIN AND ANTIBODIES THERETO

This application is a divisional of pending prior application Ser. No. 08/263,935, filed Jun. 21, 1994.

FIELD OF THE INVENTION

The present invention relates to cyclin-dependent kinase (CDK) inhibiting proteins in general, and particularly relates to DNA encoding an 18 Kilodalton inhibitor of CDK6.

BACKGROUND OF THE INVENTION

The cyclin-dependent kinases, or "CDKs", are a family of proteins involved in cell-cycle regulation. The CDKs are only active as kinases when they associate with other proteins known as cyclins, on which they are dependent. The manner by which the CDKs control cell cycle regulation has, however, only recently begun to be explained.

Y. Xiong et al., Cell 71, 505–514 (1992) showed that, in vivo in normal human fibroblasts, there exists a quaternary complex of cyclin D, p21, CDK, and proliferating cell nuclear antigen (or "PCNA"). See also H. Zhang et al., Molec. Biol. Cell 4, 897 (1993); Y. Xiong et al., Genes & Development 7, 1572 (1993). These results indicated that in addition to the cyclin activation and subunit phosphorylation, the activity of CDKs may be controlled by a number of small proteins (e.g., $p21^{WAF1/Cip1/Sdi1}$ and $p16^{INK4}$) that physically interact with cyclins, CDKs or cyclin-CDK complexes.

Y. Xiong et al., Nature 366, 701–704 (16 Dec. 1993), describes the cloning of p21 and shows that p21 is an inhibitor of cyclin kinases (p21 had previously been cloned and described as a senescent cell-derived derived inhibitor, or "sdi", by J. R. Smith, U.S. Pat. No. 5,302,706). This work and the work of others (see El-Deiry et al., Cell 75, 817–825 (1993) further shows that p21 is upregulated by the upregulation of the tumor supressor protein p53. By showing that p21 is under the control of p53, this work indicates that the p21 serves as a critical link between the tumor supressor protein p53 and the CDK cell cycle control mechanisms.

A. Kamb et al., Science 264, 436–440 (15 Apr. 1994) and T. Noborl et al., Nature 368, 753–756 (21 Apr. 1994) describe the isolation of the multiple tumor supressor 1 and 2 DNA, (or "MTS1" and "MTS2"), which encode the CDK4 inhibitor p16 (previously identified in M. Serrano et al., Nature 366, 704–707 (16 Dec. 1993)). It is suggested that both p16 and p21 are expected to antagonize entry into the S phase of the cell cycle, and that in vitro p16 appears more specific than p21.

SUMMARY OF THE INVENTION

A first aspect of the present invention is an isolated nucleic acid encoding a CDK inhibiting protein, particularly a CDK6 inhibiting protein. The nucleic acid may be selected from the group consisting of:

(a) DNA having the nucleotide sequence given herein as SEQ ID NO:1 (which encodes the protein having the amino acid sequence given herein as SEQ ID NO:2), and which we refer to as $p18^{INK6}$;

(b) nucleic acids which hybridize to DNA of (a) above (e.g., under stringent conditions) and which encode a CDK inhibiting protein; and (c) nucleic acids which differs from the DNA of (a) or (b) above due to the degeneracy of the genetic code, and which encodes a CDK inhibiting protein encoded by a DNA of (a) or (b) above.

A second aspect of the present invention is a nucleic acid construct having a promoter and a heterologous nucleic acid operably linked to said promoter, wherein said heterologous nucleic acid is a nucleic acid as given above, along with cells containing such nucleic acid constructs (e.g., wherein the cell is one which expresses the encoded protein).

A third aspect of the present invention is a protein encoded by a nucleic acid as given above. Such proteins may be isolated and/or purified in accordance with known techniques.

A fourth aspect of the present invention is an antibody (e.g., a polyclonal antibody, a monoclonal antibody) which specifically binds to a protein as given above.

A fifth aspect of the present invention is an antisense oligonucleotide complementary to a nucleic acid as given above and having a length sufficient to hybridize thereto under physiological conditions, along with DNA encoding such an antisense oligonucleotide, and a nucleic acid construct having a promoter and a heterologous nucleic acid operably linked to said promoter, wherein the heterologous nucleic acid is a DNA encoding such an antisense oligonucleotide.

A sixth aspect of the present invention is a method of inhibiting DNA synthesis in a human cell (e.g., a tumor cell) which comprises providing to the cell a protein as given above in an amount effective to inhibit DNA synthesis therein. The cell may be provided in any suitable form, such as in in vitro culture. The providing step may be carried out by any suitable means, such as by delivering the protein into the cell or by delivering into the cell a nucleic acid encoding the protein and which expresses the protein in the cell.

A seventh aspect of the present invention is a method for increasing DNA synthesis in a cell, wherein DNA synthesis in the cell is inhibited, by providing to the cell an antisense oligonucleotide as given above in an amount effective to increase DNA synthesis in said cell. The cell may be a skin cell, such as a cell present in wound or burn tissue. Again the providing step may be carried out by any suitable means, such as by delivering the antisense oligonucleotide into the cell, or by delivering into the cell a nucleic acid encoding an antisense oligonucleotide as given above and which transcribes the antisense oligonucleotide in the cell.

The foregoing and other objects and aspects of the present invention are explained in detail in the specification set forth below.

DETAILED DESCRIPTION OF THE INVENTION

Amino acid sequences disclosed herein are presented in the amino to carboxy direction, from left to right. The amino and carboxy groups are not presented in the sequence. Nucleotide sequences are presented herein by single strand only, in the 5' to 3' direction, from left to right. Nucleotides and amino acids are represented herein in the manner recommended by the IUPAC-IUB Biochemical Nomenclature Commission, or (for amino acids) by three letter code, in accordance with 37 CFR §1.822 and established usage. See, e.g., Patent In User Manual, 99–102 (November 1990) (U.S. Patent and Trademark Office).

A. DNA sequences

DNAs of the present invention include those coding for proteins homologous to, and having essentially the same biological properties as, the proteins disclosed herein, and particularly the DNA disclosed herein as SEQ ID NO:1 and encoding the protein given herein SEQ ID NO:2. This definition is intended to encompass natural allelic variations therein. Thus, isolated DNA or cloned genes of the present invention can be of any species of origin, including mouse, rat, rabbit, cat, porcine, and human, but are preferably of mammalian origin. Thus, DNAs which hybridize to DNA disclosed herein as SEQ ID NO:1 (or fragments or derivatives thereof which serve as hybridization probes as discussed below) and which code on expression for a protein of the present invention (e.g., a protein according to SEQ ID NO:2) are also an aspect of this invention (subject to the proviso that the MTS1 and MTS2 DNAs disclosed in A. Kamb et al., Science 264, 436 (1994) are excluded from this definition of the instant invention). Conditions which will permit other DNAs which code on expression for a protein of the present invention to hybridize to the DNA of SEQ ID NO:1 disclosed herein can be determined in accordance with known techniques. For example, hybridization of such sequences may be carried out under conditions of reduced stringency, medium stringency or even stringent conditions (e.g., conditions represented by a wash stringency of 35–40% Formamide with 5× Denhardt's solution, 0.5% SDS and 1× SSPE at 37° C.; conditions represented by a wash stringency of 40–45% Formamide with 5× Denhardt's solution, 0.5% SDS, and 1× SSPE at 42° C.; and conditions represented by a wash stringency of 50% Formamide with 5× Denhardt's solution, 0.5% SDS and 1×SSPE at 42° C., respectively) to DNA of SEQ ID NO:1 disclosed herein in a standard hybridization assay. See, e.g., J. Sambrook et al., Molecular Cloning, A Laboratory Manual (2d Ed. 1989) (Cold Spring Harbor Laboratory)). In general, sequences which code for proteins of the present invention and which hybridize to the DNA of SEQ ID NO:1 disclosed herein will be at least 75% homologous, 85% homologous, and even 95% homologous or more with SEQ ID NO:1. Further, DNAs which code for proteins of the present invention, or DNAs which hybridize to that of SEQ ID NO:1, but which differ in codon sequence from SEQ ID NO:1 due to the degeneracy of the genetic code, are also an aspect of this invention. The degeneracy of the genetic code, which allows different nucleic acid sequences to code for the same protein or peptide, is well known in the literature. See, e.g., U.S. Pat. No. 4,757,006 to Toole et al. at Col. 2, Table 1.

Knowledge of the nucleotide sequence as disclosed herein in SEQ ID NO:1 can be used to generate hybridization probes which specifically bind to the DNA of the present invention or to mRNA to determine the presence of amplification or overexpression of the proteins of the present invention. For example, oligonucleotide probes that are homologous to both DNA of SEQ ID NO:1 and to MTS1 or MTS2 DNA encoding p16 as described in M. Serrano et al., Nature 366, 704–707 (16 December 1993) and A. Kamb, Science 264, 436 (1994), may be used to locate homologous DNAs of the same family in the same species or other species. Examples of such probes are the probes having the sequences given herein as SEQ ID NO:3 and SEQ ID NO:4. The hybridization probes may be cDNA fragments or oligonucleotides, and may be labelled with a detectable group as discussed hereinbelow. Pairs of probes which will serve as PCR primers for the DNA sequences of the present invention, or portions thereof, may be used in accordance with the process described in U.S. Pat. Nos. 4,683,202 and 4,683,195 to Mullis (applicant specifically intends that the disclosures of all U.S. Patent references disclosed herein be incorporated herein by reference).

B. Genetic Engineering Techniques

The production of cloned genes, recombinant DNA, vectors, transformed host cells, proteins and protein fragments by genetic engineering is well known. See, e.g., U.S. Pat. No. 4,761,371 to Bell et al. at Col. 6 line 3 to Col. 9 line 65; U.S. Pat. No. 4,877,729 to Clark et al. at Col. 4 line 38 to Col. 7 line 6; U.S. Pat. No. 4,912,038 to Schilling at Col. 3 line 26 to Col. 14 line 12; and U.S. Pat. No. 4,879,224 to Wallner at Col. 6 line 8 to Col. 8 line 59. (Applicant specifically intends that the disclosure of all patent references cited herein be incorporated herein in their entirety by reference).

A vector is a replicable DNA construct. Vectors are used herein either to amplify DNA encoding the proteins of the present invention or to express the proteins of the present invention. An expression vector is a replicable DNA construct in which a DNA sequence encoding the proteins of the present invention is operably linked to suitable control sequences capable of effecting the expression of proteins of the present invention in a suitable host. The need for such control sequences will vary depending upon the host selected and the transformation method chosen. Generally, control sequences include a transcriptional promoter, an optional operator sequence to control transcription, a sequence encoding suitable mRNA ribosomal binding sites, and sequences which control the termination of transcription and translation. Amplification vectors do not require expression control domains. All that is needed is the ability to replicate in a host, usually conferred by an origin of replication, and a selection gene to facilitate recognition of transformants.

Vectors comprise plasmids, viruses (e.g., adenovirus, cytomegalovirus), phage, retroviruses and integratable DNA fragments (i.e., fragments integratable into the host genome by recombination). The vector replicates and functions independently of the host genome, or may, in some instances, integrate into the genome itself. Expression vectors should contain a promoter and RNA binding sites which are operably linked to the gene to be expressed and are operable in the host organism.

DNA regions are operably linked or operably associated when they are functionally related to each other. For example, a promoter is operably linked to a coding sequence if it controls the transcription of the sequence; a ribosome binding site is operably linked to a coding sequence if it is positioned so as to permit translation. Generally, operably linked means contiguous and, in the case of leader sequences, contiguous and in reading phase.

Transformed host cells are cells which have been transformed or transfected with vectors containing DNA coding for proteins of the present invention, constructed using recombinant DNA techniques. Transformed host cells ordinarily express protein, but host cells transformed for purposes of cloning or amplifying DNA coding for the proteins of the present invention need not express protein.

Suitable host cells include prokaryotes, yeast cells, or higher eukaryotic organism cells. Prokaryote host cells include gram negative or gram positive organisms, for example Escherichia coli (E. coli) or Bacilli. Higher eukaryotic cells include established cell lines of mammalian origin as described below. Exemplary host cells are E. coli W3110 (ATCC 27,325), E. coli B, E. coli X1776 (ATCC 31,537), E. coli 294 (ATCC 31,446). A broad variety of suitable prokaryotic and microbial vectors are available. E. coli is typically transformed using pBR322. See Bolivar et al., Gene 2, 95 (1977). Promoters most commonly used in recombinant microbial expression vectors include the beta-lactamase (penicillinase) and lactose promoter systems (Chang et al., Nature 275, 615 (1978); and Goeddel et al., Nature 281, 544 (1979)), a tryptophan (trp) promoter system (Goeddel et al., *Nucleic Acids Res.* 8, 4057 (1980) and EPO App. Publ. No. 36,776) and the tac promoter (H. De Boer et al., *Proc. Natl. Acad. Sci. USA* 80, 21 (1983)). The promoter and Shine-Dalgarno sequence (for prokaryotic host expression) are operably linked to the DNA of the present invention, i.e., they are positioned so as to promote transcription of the messenger RNA from the DNA.

Expression vectors should contain a promoter which is recognized by the host organism. This generally means a promoter obtained from the intended host. Promoters most commonly used in recombinant microbial expression vectors include the beta-lactamase (penicillinase) and lactose promoter systems (Chang et al., *Nature* 275, 615 (1978); and Goeddel et al., *Nature* 281, 544 (1979)), a tryptophan (trp) promoter system (Goeddel et al., *Nucleic Acids Res.* 8, 4057 (1980) and EPO App. Publ. No. 36,776) and the tac promoter (H. De Boer et al., *Proc. Natl. Acad. Sci. USA* 80, 21 (1983)). While these are commonly used, other microbial promoters are suitable. Details concerning nucleotide sequences of many have been published, enabling a skilled worker to operably ligate them to DNA encoding the protein in plasmid or viral vectors (Siebenlist et al., *Cell* 20, 269 (1980)). The promoter and Shine-Dalgarno sequence (for prokaryotic host expression) are operably linked to the DNA encoding the desired protein, i.e., they are positioned so as to promote transcription of the protein messenger RNA from the DNA.

Eukaryotic microbes such as yeast cultures may be transformed with suitable protein-encoding vectors. See, e.g., U.S. Pat. No. 4,745,057. *Saccharomyces cerevisiae* is the most commonly used among lower eukaryotic host microorganisms, although a number of other strains are commonly available. Yeast vectors may contain an origin of replication from the 2 micron yeast plasmid or an autonomously replicating sequence (ARS), a promoter, DNA encoding the desired protein, sequences for polyadenylation and transcription termination, and a selection gene. An exemplary plasmid is YRp7, (Stinchcomb et al., *Nature* 282, 39 (1979); Kingsman et al., *Gene* 7, 141 (1979); Tschemper et al., *Gene* 10, 157 (1980)). This plasmid contains the trp1 gene, which provides a selection marker for a mutant strain of yeast lacking the ability to grow in tryptophan, for example ATCC No. 44076 or PEP4-1 (Jones, *Genetics* 85, 12 (1977)). The presence of the trp1 lesion in the yeast host cell genome then provides an effective environment for detecting transformation by growth in the absence of tryptophan.

Suitable promoting sequences in yeast vectors include the promoters for metallothionein, 3-phosphoglycerate glycerate kinase (Hitzeman et al., *J. Biol. Chem.* 255, 2073 (1980) or other glycolytic enzymes (Hess et al., *J. Adv. Enzyme Reg.* 7, 149 (1968); and Holland et al., *Biochemistry* 17, 4900 (1978)), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Suitable vectors and promoters for use in yeast expression are further described in R. Hitzeman et al., EPO Publn. No. 73,657.

Cultures of cells derived from multicellular organisms are a desirable host for recombinant protein synthesis. In principal, any higher eukaryotic cell culture is workable, whether from vertebrate or invertebrate culture, including insect cells. Propagation of such cells in cell culture has become a routine procedure. See Tissue Culture, Academic Press, Kruse and Patterson, editors (1973). Examples of useful host cell lines are VERO and HeLa cells, Chinese hamster ovary (CHO) cell lines, and WI138, BHK, COS-7, CV, and MDCK cell lines. Expression vectors for such cells ordinarily include (if necessary) an origin of replication, a promoter located upstream from the gene to be expressed, along with a ribosome binding site, RNA splice site (if intron-containing genomic DNA is used), a polyadenylation site, and a transcriptional termination sequence.

The transcriptional and translational control sequences in expression vectors to be used in transforming vertebrate cells are often provided by viral sources. For example, commonly used promoters are derived from polyoma, Adenovirus 2, and Simian Virus 40 (SV40). See, e.g., U.S. Pat. No. 4,599,308. The early and late promoters are useful because both are obtained easily from the virus as a fragment which also contains the SV40 viral origin of replication. See Fiers et al., *Nature* 273, 113 (1978). Further, the protein promoter, control and/or signal sequences, may also be used, provided such control sequences are compatible with the host cell chosen.

An origin of replication may be provided either by construction of the vector to include an exogenous origin, such as may be derived from SV40 or other viral source (e.g. Polyoma, Adenovirus, VSV, or BPV), or may be provided by the host cell chromosomal replication mechanism. If the vector is integrated into the host cell chromosome, the latter may be sufficient.

Host cells such as insect cells (e.g., cultured *Spodoptera frugiperda* cells) and expression vectors such as the baculovirus expression vector (e.g., vectors derived from *Autographa californica* MNPV, *Trichoplusia ni* MNPV, *Rachiplusia ou* MNPV, or *Galleria ou* MNPV) may be employed to make proteins useful in carrying out the present invention, as described in U.S. Pat. Nos. 4,745,051 and 4,879,236 to Smith et al. In general, a baculovirus expression vector comprises a baculovirus genome containing the gene to be expressed inserted into the polyhedrin gene at a position ranging from the polyhedrin transcriptional start signal to the ATG start site and under the transcriptional control of a baculovirus polyhedrin promoter.

Rather than using vectors which contain viral origins of replication, one can transform mammalian cells by the method of cotransformation with a selectable marker and the chimeric protein DNA. An example of a suitable selectable marker is dihydrofolate reductase (DHFR) or thymidine kinase. See U.S. Pat. No. 4,399,216. Such markers are proteins, generally enzymes, that enable the identification of transformant cells, i.e., cells which are competent to take up exogenous DNA. Generally, identification is by survival of transformants in culture medium that is toxic, or from which the cells cannot obtain critical nutrition without having taken up the marker protein.

C. Ligand Analogs and Mimetics

As used herein, "ligand" refers to a molecule that is recognized by a particular receptor protein. With reference to the present invention, a ligand is a molecule, such as a peptide, that is specifically binds to CDK6 at the site bound by the protein having the sequence given herein as SEQ ID NO:2 and competes with that protein for binding to that site. As used herein, an "inhibitory ligand" or an "inhibitory binding ligand" is a ligand which binds to and inhibits the normal activity of the receptor protein. "Receptor" refers to a molecule that has an affinity for a given ligand.

Analogs of $p18^{INK6}$ ligands are an aspect of the present invention. As used herein, an "analog" is a chemical compound similar in structure to a first compound, and having either a similar or opposite physiologic action as the first compound. With particular reference to the present invention, p18$^{INK6}$ ligand analogs are those compounds which, while not having the amino acid sequences of native p18$^{INK6}$ ligands, are capable of binding to p18$^{INK6}$. Such analogs may be peptide or non-peptide analogs, including nucleic acid analogs, as described in further detail below.

In protein molecules which interact with a receptor, the interaction between the protein and the receptor must take place at surface-accessible sites in a stable three-dimensional molecule. By arranging the critical binding site residues in an appropriate conformation, peptides which mimic the essential surface features of the p18$^{INK6}$ ligands may be designed and synthesized in accordance with known techniques.

Methods for determining peptide three-dimensional structure and analogs thereto are known, and are sometimes referred to as "rational drug design techniques". See, e.g., U.S. Pat. No. 4,833,092 to Geysen; U.S. Pat. No. 4,859,765 to Nestor; U.S. Pat. No. 4,853,871 to Pantoliano; U.S. Pat. No. 4,863,857 to Blalock; (applicants specifically intend that the disclosure of all U.S. Patent references cited herein be incorporated by reference herein in their entirety). See also Waldrop, *Science*, 247, 28029 (1990); Rossmann, *Nature*, 333, 392–393 (1988); Weis et al., *Nature*, 333, 426–431 (1988); James et al., *Science*, 260, 1937 (1993) (development of benzodiazepine peptidomimetic compounds based on the structure and function of tetrapeptide ligands).

In general, those skilled in the art will appreciate that minor deletions or substitutions may be made to the amino acid sequences of peptides of the present invention without unduly adversely affecting the activity thereof. Thus, peptides containing such deletions or substitutions are a further aspect of the present invention. In peptides containing substitutions or replacements of amino acids, one or more amino acids of a peptide sequence may be replaced by one or more other amino acids wherein such replacement does not affect the function of that sequence. Such changes can be guided by known similarities between amino acids in physical features such as charge density, hydrophobicity/hydrophilicity, size and configuration, so that amino acids are substituted with other amino acids having essentially the same functional properties. For example: Ala may be replaced with Val or Ser; Val may be replaced with Ala, Leu, Met, or Ile, preferably Ala or Leu; Leu may be replaced with Ala, Val or Ile, preferably Val or Ile; Gly may be replaced with Pro or Cys, preferably Pro; Pro may be replaced with Gly, Cys, Ser, or Met, preferably Gly, Cys, or Ser; Cys may be replaced with Gly, Pro, Ser, or Met, preferably Pro or Met; Met may be replaced with Pro or Cys, preferably Cys; His may be replaced with Phe or Gln, preferably Phe; Phe may be replaced with His, Tyr, or Trp, preferably His or Tyr; Tyr may be replaced with His, Phe or Trp, preferably Phe or Trp; Trp may be replaced with Phe or Tyr, preferably Tyr; Asn may be replaced with Gln or Ser, preferably Gln; Gln may be replaced with His, Lys, Glu, Ash, or Ser, preferably Asn or Ser; Ser may be replaced with Gln, Thr, Pro, Cys or Ala; Thr may be replaced with Gln or Ser, preferably Ser; Lys may be replaced with Gln or Arg; Arg may be replaced with Lys, Asp or Glu, preferably Lys or Asp; Asp may be replaced with Lys, Arg, or Glu, preferably Arg or Glu; and Glu may be replaced with Arg or Asp, preferably Asp. Once made, changes can be routinely screened to determine their effects on function with enzymes.

Non-peptide mimetics of the peptides of the present invention are also an aspect of this invention. Non-protein drug design may be carried out using computer graphic modeling to design non-peptide, organic molecules which bind to sites bound by p18$^{INK6}$. See, e.g., Knight, *BIO/Technology*, 8, 105 (1990). Itzstein et al, *Nature*, 363, 418 (1993) (peptidomimetic inhibitors of influenza virus enzyme, sialidase). Itzstein et al modeled the crystal structure of the sialidase receptor protein using data from x-ray crystallography studies and developed an inhibitor that would attach to active sites of the model; the use of nuclear magnetic resonance (NMR) data for modeling is also known in the art. See also Lam et al, *Science*, 263, 380 (January 1994) regarding the rational design of bioavailable nonpeptide cyclic ureas that function as HIV protease inhibitors. Lam et al used information from x-ray crystal structure studies of HIV protease inhibitor complexes to design non-peptide inhibitors.

The modeling of a protein kinase structure using the known structure of other kinases is reported by Knighton et al., *Science*, 258, 130 (1992) (smooth muscle myosin light chain kinase catalytic core modeled using crystallography data of cyclic AMP-dependent protein kinase catalytic subunit and a bound pseudosubstrate inhibitor). See also Marcote et al., *Mol. Cell. Biol.*, 13, 5122 (1993) (crystallography data of cyclic AMP dependent protein kinase used to model Cdc2 protein kinase); Knighton et al., *Science*, 253, 407 (1991); Knighton et al., *Science*, 253, 414 (1991); DeBondt et al., *Nature*, 363, 595 (1993) (crystal structure of human CDK2 kinase determined).

Analogs may also be developed by generating a library of molecules, selecting for those molecules which act as ligands for a specified target, and identifying and amplifying the selected ligands. See, e.g., Kohl et al., *Science*, 260, 1934 (1993) (synthesis and screening of tetrapeptides for inhibitors of farnesyl protein transferase, to inhibit ras oncoprotein dependent cell transformation). Techniques for constructing and screening combinatorial libraries of oligomeric biomolecules to identify those that specifically bind to a given receptor protein are known. Suitable oligomers include peptides, oligonucleotides, carbohydrates, nonoligonucleotides (e.g., phosphorothioate oligonucleotides; see *Chem. and Engineering News*, page 20, 7 Feb. 1994) and nonpeptide polymers (see, e.g., "peptoids" of Simon et al., *Proc. Natl. Acad. Sci. USA*, 89, 9367 (1992)). See also U.S. Pat. No. 5,270,170 to Schatz; Scott and Smith, *Science*, 249, 386–390 (1990); Devlin et al., *Science* 249,404–406 (1990); Edgington, *BIO/Technology*, 11, 285 (1993). Peptide libraries may be synthesized on solid supports, or expressed on the surface of bacteriophage viruses (phage display libraries). Known screening methods may be used by those skilled in the art to screen combinatorial libraries to identify ligand analogs of p18$^{INK6}$. Techniques are known in the art for screening synthesized molecules to select those with the desired activity, and for labelling the members of the library so that selected active molecules may be identified. See, e.g., Brenner and Lerner, *Proc. Natl. Acad. Sci. USA*, 89, 5381 (1992) (use of genetic tag to label molecules in a combinatorial library); PCT US93/06948 to Berger et al., (use of recombinant cell transformed with vital transactivating element to screen for potential antiviral molecules able to inhibit initiation of vital transcription); Simon et al., *Proc. Natl. Acad. Sci. USA*, 89, 9367, (1992) (generation and screening of "peptoids", oligomeric N-substituted glycines, to identify ligands for biological receptors); U.S. Pat. No. 5,283,173 to Fields et al., (use of genetically altered *Saccharomyces cerevisiae* to screen peptides for interactions).

As used herein, "combinatorial library" refers to collections of diverse oligomeric biomolecules of differing sequence, which can be screened simultaneously for activity as a ligand for a particular target. Combinatorial libraries may also be referred to as "shape libraries", i.e., a population of randomized polymers which are potential ligands. The shape of a molecule refers to those features of a molecule that govern its interactions with other molecules, including Van der Waals, hydrophobic, electrostatic and dynamic.

Nucleic acid molecules may also act as ligands for receptor proteins. See, e.g., Edgington, *BIO/Technology,* 11, 285 (1993). U.S. Pat. No. 5,270,163 to Gold and Tuerk describes a method for identifying nucleic acid ligands for a given target molecule by selecting from a library of RNA molecules with randomized sequences those molecules that bind specifically to the target molecule. A method for the in vitro selection of RNA molecules immunologically cross-reactive with a specific peptide is disclosed in Tsai, Kenan and Keene, *Proc. Natl. Acad. Sci. USA,* 89, 8864 (1992) and Tsai and Keene, *J. Immunology,* 150, 1137 (1993). In the method, an antiserum raised against a peptide is used to select RNA molecules from a library of RNA molecules; selected RNA molecules and the peptide compete for antibody binding, indicating that the RNA epitope functions as a specific inhibitor of the antibody-antigen interaction.

C. Use of the Receptors and Proteins

As noted above, the present invention provides isolated and purified $p18^{INK6}$ receptor proteins, such as mammalian (or more preferably human) $p18^{INK6}$ receptor proteins. Such proteins can be purified from host cells which express the same, in accordance with known techniques, or even manufactured synthetically.

DNAs of the present invention, constructs containing the same and host cells that express the encoded proteins are useful for making proteins of the present invention.

Proteins of the present invention are useful as immunogens for making antibodies as described herein, and these antibodies and proteins provide a "specific binding pair." Such specific binding pairs are useful as components of a variety of immunoassays and purification techniques, as is known in the art.

The proteins of the present invention are of known amino acid sequence as disclosed herein, and hence are useful as molecular weight markers in determining the molecular weights of proteins of unknown structure.

The DNAs, proteins and mimetics of the present invention can be used in a similar manner as the DNA and proteins of U.S. Pat. No. 5,302,706 to Smith, the disclosure of which is incorporated herein by reference in its entirety.

Antibodies. Antibodies which specifically bind to the proteins of the present invention (i.e., antibodies which bind to a single antigenic site or epitope on the proteins) are useful for a variety of diagnostic purposes. Such antibodies may be polyclonal or monoclonal in origin, but are preferably of monoclonal origin. The antibodies are preferably IgG antibodies of any suitable species, such as rat, rabbit, or horse, but are generally of mammalian origin. Fragments of IgG antibodies which retain the ability to specifically bind the proteins of the present invention, such as $F(ab')_2$, F(ab'), and Fab fragments, are intended to be encompassed by the term "antibody" herein. See generally E. Harlow and D. Lane, Antibodies: A Laboratory Manual (1988)(New York: Cold Spring Harbor Laboratory Press). The antibodies may be chimeric, as described by M. Walker et al., *Molecular Immunol.* 26, 403 (1989).

Monoclonal antibodies which bind to proteins of the present invention are made by culturing a cell or cell line capable of producing the antibody under conditions suitable for the production of the antibody (e.g., by maintaining the cell line in HAT media), and then collecting the antibody from the culture (e.g., by precipitation, ion exchange chromatography, affinity chromatography, or the like). The antibodies may be generated in a hybridoma cell line in the widely used procedure described by G. Kohler and C. Milstein, *Nature* 256, 495 (1975), or may be generated with a recombinant vector in a suitable host cell such as *Escherichia coli* in the manner described by W. Huse et al., *Science* 246, 1275 (1989).

Immunoassays. Assays for detecting expression of proteins of the present invention in a cell or the extent of expression thereof generally comprise the steps of, first, contacting cells or extracts of cells to antibodies capable of specifically binding the proteins, and determining the extent of binding of said antibodies to said cells. The antibody is preferably labelled, as discussed above, to facilitate the detection of binding. Any suitable immunoassay procedure may be employed, such as radioimmunoassay, immunofluorescence, precipitation, agglutination, complement fixation, and enzyme-linked immunosorbent assay. When the cells to be tested remain within the body of a mammal, the antibodies are labelled with a radioactive detectable group and administered to the mammal, and the extent of binding of the antibodies to the cells is observed by external scanning for radioactivity. As discussed above, while any type of antibody may be employed for the foregoing diagnostic purposes, monoclonal antibodies are preferred. Those skilled in the art will be familiar with numerous specific immunoassay formats and variations thereof which may be useful for carrying out the method disclosed herein. See generally E. Harlow and D. Lane, supra; E. Maggio, *Enzyme-Immunoassay,* (1980) (CRC Press, Inc., Boca Raton, Fla.); see also U.S. Pat. No. 4,727,022 to Skold et al.; U.S. Pat. No. 4,659,678 to Forrest et al., U.S. Pat. No. 4,376,110 to David et al., U.S. Pat. No. 4,275,149 to Litman et al., U.S. Pat. No. 4,233,402 to Maggio et al., and U.S. Pat. No. 4,230,767 to Boguslaski et al.

Antibodies may be conjugated to a solid support suitable for a diagnostic assay (e.g., beads, plates, slides or wells formed from materials such as latex or polystyrene) in accordance with known techniques, such as precipitation. Antibodies may likewise be conjugated to detectable groups such as radiolabels (e.g., $^{35}S$, $^{125}I$, $^{131}I$), enzyme labels (e.g., horseradish peroxidase, alkaline phosphatase), and fluorescent labels (e.g., fluorescein) in accordance with known techniques.

Kits for determining if a sample contains proteins of the present invention will include at least one reagent specific for detecting the presence or absence of the protein. Diagnostic kits for carrying out antibody assays may be produced in a number of ways. In one embodiment, the diagnostic kit comprises (a) an antibody which binds proteins of the present invention conjugated to a solid support and (b) a second antibody which binds proteins of the present invention conjugated to a detectable group. The reagents may also include ancillary agents such as buffering agents and protein stabilizing agents, e.g., polysaccharides and the like. The diagnostic kit may further include, where necessary, other members of the signal-producing system of which system the detectable group is a member (e.g., enzyme substrates), agents for reducing background interference in a test, control reagents, apparatus for conducting a test, and the like. A second embodiment of a test kit comprises (a) an antibody as above, and (b) a specific binding partner for the antibody conjugated to a detectable group. Ancillary agents as described above may likewise be included. The test kit may be packaged in any suitable manner, typically with all elements in a single container along with a sheet of printed instructions for carrying out the test.

Nucleic Acid Assays. Assays for detecting $p18^{INK6}$ DNA or mRNA in a cell, or the extent of amplification thereof, typically involve, first, contacting the cells or extracts of the cells containing nucleic acids therefrom with an oligonucleotide that specifically binds to $p18^{INK6}$ DNA or mRNA as given herein (typically under conditions that permit access of the oligonucleotide to intracellular material), and then detecting the presence or absence of binding of the oligonucleotide thereto. Again, any suitable assay format may be employed (see, e.g., U.S. Pat. No. 4,358,535 to Falkow et al.; U.S. Pat. No. 4,302,204 to Wahl et al.; U. S. Pat. No. 4,994,373 to Stavrianopoulos et al; U.S. Pat. No. 4,486,539 to Ranki et al.; U.S. Pat. No. 4,563,419 to Ranki et al.; and U.S. Pat. No. 4,868,104 to Kurn et al.)(the disclosures of which applicant specifically intends be incorporated herein by reference).

Antisense Oligonucleotides. Antisense oligonucleotides and nucleic acids that express the same may be made in accordance with conventional techniques. See, e.g., U.S. Pat. No. 5,023,243 to Tullis; U.S. Pat. No. 5,149,797 to Pederson et al. The length of the antisense oligonucleotide (i.e., the number of nucleotides therein) is not critical so long as it binds selectively to the intended location, and can be determined in accordance with routine procedures. In general, the antisense oligonucleotide will be from 8, 10 or 12 nucleotides in length up to 20, 30, or 50 nucleotides in length. Such antisense oligonucleotides may be oligonucleotides wherein at least one, or all, of the internucleotide bridging phosphate residues are modified phosphates, such as methyl phosphonates, methyl phosphonothioates, phosphoromorpholidates, phosphoropiperazidates and phosphoramidates. For example, every other one of the internucleotide bridging phosphate residues may be modified as described. In another non-limiting example, such antisense oligonucleotides are oligonucleotides wherein at least one, or all, of the nucleotides contain a 2' loweralkyl moiety (e.g., C1–C4, linear or branched, saturated or unsaturated alkyl, such as methyl, ethyl, ethenyl, propyl, 1-propenyl, 2-propenyl, and isopropyl). For example, every other one of the nucleotides may be modified as described. See also P. Furdon et al., Nucleic Acids Res. 17, 9193–9204 (1989); S. Agrawal et al., Proc. Natl. Acad. Sci. USA 87, 1401–1405 (1990); C. Baker et al., Nucleic Acids Res. 18, 3537–3543 (1990); B. Sproat et al., Nucleic Acids Res. 17, 3373–3386 (1989); R. Walder and J. Walder, Proc. Natl. Acad. Sci. USA 85, 5011–5015 (1988).

The following examples are provided to illustrate the present invention, and should not be construed as limiting thereof. In these examples, D means Dalton, kD means kilodalton, mM means milliMolar, and temperatures are given in degrees Centigrade unless otherwise indicated.

EXAMPLE 1

Isolation of $p18^{INK6}$

Human $p18^{INK6}$ was isolated by two-hybrid screening (Fields and Song, Nature 340:245–246 (1989) as follows. The complete open reading frame of human cyclin-dependent kinase 6 (CDK6; Meyerson et al., EMBO J., 11, 2909–2917 (1992)) was inserted into the vector pGBT8 (constructed by Y. Xiong), a modified form of the yeast two hybrid screening vector pGBT9 (constructed by S. Field) which directs the expression of a fusion between the DNA-binding domain (amino acids 1–147) of Gal-4 and the entire CDK6 protein from a crippled ADH promoter. This plasmid, which also contains a TRP1 marker, was co-transformed into yeast strain Y190 (W. Harper et al., Cell 75, 805–816 (1993)) with the human HeLa cDNA library constructed in vector pGADGL (Clontech Inc.) that carries a Leu marker. Transformants were plated on yeast drop-out media lacking leucine, tryptophan, and histidine, and containing 30 mM 3-amino-1,2,4 triazole (3-AT). An estimated $5 \times 10^6$ transformants were screened. After 6 days of growth, histidine positive (His+) colonies were tested for b-galactosidase activity. Forty-five colonies were positive for b-galactosidase staining and were further purified on selective media. Plasmid DNA was recovered from positive colonies and introduced into Escherichia coli strain JM101 (J. Messing, Recomb. DNA Tech. bull. 2(2): 43 (1979)).

The cDNAs from plasmids recovered from E. coli were excised from pGADGL vector and inserted into pBluescript (Stratagene Inc.). The first three hundred nucleotide sequences were determined for each clone. Most clones corresponded to the previously reported $p16^{INK4/MTS1}$. In addition to $p16^{INK4}$, a clone (6H10) was isolated that encoded a novel protein that was not present in the current data base ((GenBank release 82.00 April 1994).

A cDNA insert from clone 6H10 was used as probe to screen a human HeLa cDNA library constructed in λZAP II vector (STRATAGENE Inc.) to obtain full length sequences. More than twenty lambda clones were isolated from this screening and several of them were analyzed by DNA sequencing. One clone, H18, was determined to contain a full length coding region, as there was an in-frame stop codon located 6 base-pairs upstream of a putative initiation ATG codon. The translation of clone H18 contained 168 amino acid residues with a calculated molecular weight of 18116 D (or 18 kDa, p18) and showed 40% protein sequence similarity to $p16^{INK4/MTS1}$. This protein was named $p18^{INK6}$, following the existing nomenclature and because of the preferential interaction of $p18^{INK6}$ with CDK6.

The foregoing is illustrative of the present invention and is not to be construed as limiting thereof. The invention is defined by the following claims, with equivalents of the claims to be included therein.

That which is claimed is:

1. An antibody which specifically binds to a protein encoded by a DNA having the nucleotide sequence given herein as SEQ ID NO: 1; or fragments thereof.

2. An antibody according to claim 1, which antibody is a polyclonal antibody.

3. An antibody according to claim 1, which antibody is a monoclonal antibody.

4. An antibody which specifically binds to a protein having the amino acid sequence given herein as SEQ ID NO:2.

5. An antibody according to claim 4, which antibody is a polyclonal antibody.

6. An antibody according to claim 4, which antibody is a monoclonal antibody.

\* \* \* \* \*

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:

( A ) LENGTH: 634 base pairs ( B ) TYPE: nucleic acid ( C ) STRANDEDNESS: single
( D ) TOPOLOGY: linear ( i i ) MOLECULE TYPE: DNA (genomic)

( i x ) FEATURE:
( A ) NAME/KEY: CDS
( B ) LOCATION: 94..597

( x i ) SEQUENCE DESCRIPTION: SEQ ID NO:1:

| | | | | |
|---|---|---|---|---|
| CCGATGCCAT CATGCAGCCT GGTTAGGAGC AAAGGAAAGG GGAAAAAGAA AAACGACTAA | | | | 60 |

| | | | | | | | | | | | | | |
|---|---|---|---|---|---|---|---|---|---|---|---|---|---|
| TTCATCTTTT CCTGATCGTC AGGACCCTAA AGA | | | ATG<br>Met<br>1 | GCC<br>Ala | GAG<br>Glu | CCT<br>Pro | TGG<br>Trp | GGG<br>Gly<br>5 | AAC<br>Asn | | | 114 |

| | | | | | | | | | | | | | | | | |
|---|---|---|---|---|---|---|---|---|---|---|---|---|---|---|---|---|
| GAG<br>Glu | TTG<br>Leu | GCG<br>Ala<br>10 | TCC<br>Ser | GCA<br>Ala | GCT<br>Ala | GCC<br>Ala | AGG<br>Arg<br>15 | GGG<br>Gly | GAC<br>Asp | CTA<br>Leu | GAG<br>Glu | CAA<br>Gln<br>20 | CTT<br>Leu | ACT<br>Thr | AGT<br>Ser | 162 |

| | | | | | | | | | | | | | | | | |
|---|---|---|---|---|---|---|---|---|---|---|---|---|---|---|---|---|
| TTG<br>Leu | TTG<br>Leu<br>25 | CAA<br>Gln | AAT<br>Asn | AAT<br>Asn | GTA<br>Val | AAC<br>Asn<br>30 | GTC<br>Val | AAT<br>Asn | GCA<br>Ala | CAA<br>Gln | AAT<br>Asn<br>35 | GGA<br>Gly | TTT<br>Phe | GGA<br>Gly | AGG<br>Arg | 210 |

| | | | | | | | | | | | | | | | | |
|---|---|---|---|---|---|---|---|---|---|---|---|---|---|---|---|---|
| ACT<br>Thr<br>40 | GCG<br>Ala | CTG<br>Leu | CAG<br>Gln | GTT<br>Val | ATG<br>Met<br>45 | AAA<br>Lys | CTT<br>Leu | GGA<br>Gly | AAT<br>Asn | CCC<br>Pro<br>50 | GAT<br>Asp | ATT<br>Ile | GCC<br>Ala | AGG<br>Arg | AGA<br>Arg<br>55 | 258 |

| | | | | | | | | | | | | | | | | |
|---|---|---|---|---|---|---|---|---|---|---|---|---|---|---|---|---|
| CTG<br>Leu | CTA<br>Leu | CTT<br>Leu | AGA<br>Arg | GGT<br>Gly<br>60 | GCT<br>Ala | AAT<br>Asn | CCC<br>Pro | GAT<br>Asp | TTG<br>Leu<br>65 | AAA<br>Lys | GAC<br>Asp | CGA<br>Arg | ACT<br>Thr | GGT<br>Gly<br>70 | TTC<br>Phe | 306 |

| | | | | | | | | | | | | | | | | |
|---|---|---|---|---|---|---|---|---|---|---|---|---|---|---|---|---|
| GCT<br>Ala | GTC<br>Val | ATT<br>Ile<br>75 | CAT<br>His | GAT<br>Asp | GCG<br>Ala | GCC<br>Ala | AGA<br>Arg<br>80 | GCA<br>Ala | GGT<br>Gly | TTC<br>Phe | CTG<br>Leu | GAC<br>Asp<br>85 | ACT<br>Thr | TTA<br>Leu | CAG<br>Gln | 354 |

| | | | | | | | | | | | | | | | | |
|---|---|---|---|---|---|---|---|---|---|---|---|---|---|---|---|---|
| ACT<br>Thr | TTG<br>Leu | CTG<br>Leu<br>90 | GAG<br>Glu | TTT<br>Phe | CAA<br>Gln | GCT<br>Ala | GAT<br>Asp<br>95 | GTT<br>Val | AAC<br>Asn | ATC<br>Ile | GAG<br>Glu | GAT<br>Asp<br>100 | AAT<br>Asn | GAA<br>Glu | GGG<br>Gly | 402 |

| | | | | | | | | | | | | | | | | |
|---|---|---|---|---|---|---|---|---|---|---|---|---|---|---|---|---|
| AAC<br>Asn | CTG<br>Leu | CCC<br>Pro<br>105 | TTG<br>Leu | CAC<br>His | TTG<br>Leu | GCT<br>Ala | GCC<br>Ala<br>110 | AAA<br>Lys | GAA<br>Glu | GGC<br>Gly | CAC<br>His | CTC<br>Leu<br>115 | CGG<br>Arg | GTG<br>Val | GTG<br>Val | 450 |

| | | | | | | | | | | | | | | | | |
|---|---|---|---|---|---|---|---|---|---|---|---|---|---|---|---|---|
| GAG<br>Glu<br>120 | TTC<br>Phe | CTG<br>Leu | GTG<br>Val | AAG<br>Lys | CAC<br>His<br>125 | ACG<br>Thr | GCC<br>Ala | AGC<br>Ser | AAT<br>Asn | GTG<br>Val<br>130 | GGG<br>Gly | CAT<br>His | CGG<br>Arg | AAC<br>Asn | CAT<br>His<br>135 | 498 |

| | | | | | | | | | | | | | | | | |
|---|---|---|---|---|---|---|---|---|---|---|---|---|---|---|---|---|
| AAG<br>Lys | GGG<br>Gly | GAC<br>Asp | ACC<br>Thr<br>140 | GCC<br>Ala | TGT<br>Cys | GAT<br>Asp | TTG<br>Leu | GCC<br>Ala<br>145 | AGG<br>Arg | CTC<br>Leu | TAT<br>Tyr | GGG<br>Gly | AGG<br>Arg<br>150 | AAT<br>Asn | GAG<br>Glu | 546 |

| | | | | | | | | | | | | | | | | |
|---|---|---|---|---|---|---|---|---|---|---|---|---|---|---|---|---|
| GTT<br>Val | GTT<br>Val | AGC<br>Ser | CTG<br>Leu<br>155 | ATG<br>Met | CAG<br>Gln | GCA<br>Ala | AAC<br>Asn | GGG<br>Gly<br>160 | GCT<br>Ala | GGG<br>Gly | GGA<br>Gly | GCC<br>Ala | ACA<br>Thr<br>165 | AAT<br>Asn | CTT<br>Leu | 594 |

| | |
|---|---|
| CAA TAACGTGGGG AGGGCTCCCC CACGTTGCCT CTAAAAA<br>Gln | 634 |

( 2 ) INFORMATION FOR SEQ ID NO:2:

( i ) SEQUENCE CHARACTERISTICS:
( A ) LENGTH: 168 amino acids
( B ) TYPE: amino acid
( D ) TOPOLOGY: linear ( i i ) MOLECULE TYPE: protein ( x i ) SEQUENCE DESCRIPTION: SEQ ID NO:2:

| | | | | | | | | | | | | | | | |
|---|---|---|---|---|---|---|---|---|---|---|---|---|---|---|---|
| Met<br>1 | Ala | Glu | Pro | Trp<br>5 | Gly | Asn | Glu | Leu | Ala<br>10 | Ser | Ala | Ala | Ala | Arg<br>15 | Gly |

| | | | | | | | | | | | | | | | |
|---|---|---|---|---|---|---|---|---|---|---|---|---|---|---|---|
| Asp | Leu | Glu | Gln<br>20 | Leu | Thr | Ser | Leu | Leu<br>25 | Gln | Asn | Asn | Val | Asn<br>30 | Val | Asn |

| | | | | | | | | | | | | | | | |
|---|---|---|---|---|---|---|---|---|---|---|---|---|---|---|---|
| Ala | Gln | Asn<br>35 | Gly | Phe | Gly | Arg | Thr<br>40 | Ala | Leu | Gln | Val | Met<br>45 | Lys | Leu | Gly |

```
Asn Pro Asp Ile Ala Arg Arg Leu Leu Leu Arg Gly Ala Asn Pro Asp
    50              55                  60

Leu Lys Asp Arg Thr Gly Phe Ala Val Ile His Asp Ala Ala Arg Ala
65              70                  75                      80

Gly Phe Leu Asp Thr Leu Gln Thr Leu Leu Glu Phe Gln Ala Asp Val
            85              90                      95

Asn Ile Glu Asp Asn Glu Gly Asn Leu Pro Leu His Leu Ala Ala Lys
            100             105                     110

Glu Gly His Leu Arg Val Val Glu Phe Leu Val Lys His Thr Ala Ser
        115             120                 125

Asn Val Gly His Arg Asn His Lys Gly Asp Thr Ala Cys Asp Leu Ala
    130             135                 140

Arg Leu Tyr Gly Arg Asn Glu Val Val Ser Leu Met Gln Ala Asn Gly
145             150                 155                     160

Ala Gly Gly Ala Thr Asn Leu Gln
            165
```

(2) INFORMATION FOR SEQ ID NO:3:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

TNGCATCNGC AGCAGCACGN GG          22

(2) INFORMATION FOR SEQ ID NO:4:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

CACGACGCAG CACGNGCAGG NTTCCTNGAC ACNCT          35